United States Patent
Kneupper et al.

(10) Patent No.: US 8,298,500 B2
(45) Date of Patent: Oct. 30, 2012

(54) PROCESS AND APPARATUS FOR PRODUCING AND PURIFYING EPICHLOROHYDRINS

(75) Inventors: Christian D. Kneupper, Brazoria, TX (US); Perry S. Basile, Lake Jackson, TX (US); William W. Fan, Lake Jackson, TX (US); Sascha Noormann, Gruenendeich (DE)

(73) Assignee: Dow Global Technologies LLC, Midland, MI (US)

( * ) Notice: Subject to any disclaimer, the term of this patent is extended or adjusted under 35 U.S.C. 154(b) by 218 days.

(21) Appl. No.: 12/866,370

(22) PCT Filed: Jan. 22, 2009

(86) PCT No.: PCT/US2009/031630
§ 371 (c)(1),
(2), (4) Date: Aug. 5, 2010

(87) PCT Pub. No.: WO2009/108419
PCT Pub. Date: Sep. 3, 2009

(65) Prior Publication Data
US 2010/0331555 A1   Dec. 30, 2010

Related U.S. Application Data

(60) Provisional application No. 61/067,324, filed on Feb. 27, 2008, provisional application No. 61/031,570, filed on Feb. 26, 2008.

(51) Int. Cl.
*B01J 8/00* (2006.01)
*C07D 301/26* (2006.01)
(52) U.S. Cl. ........................ 422/608; 549/520
(58) Field of Classification Search ............. 422/608; 549/520
See application file for complete search history.

(56) References Cited

U.S. PATENT DOCUMENTS

| 4,944,847 A | 7/1990 | Snow |
| 4,952,647 A | 8/1990 | Shirtum et al. |
| 5,344,945 A | 9/1994 | Grunchard |

FOREIGN PATENT DOCUMENTS

| DE | 197308 | 4/1908 |
| DE | 1285993 B | 1/1969 |
| GB | 974164 | 11/1964 |
| GB | 2173496 A | 10/1986 |
| JP | 60-258172 | 12/1985 |
| WO | 2005021476 A1 | 3/2005 |
| WO | 2006020234 A1 | 2/2006 |
| WO | 2008087657 A | 7/2008 |

OTHER PUBLICATIONS

Perry's Chemical Engineers' Handbook, Sixth Ed., 1984, McGraw Hill Book Company, XP002520495, pp. 13-9-pp. 13-10.
Carra, S., et al., Synlhesis of Epichlorohydrin by Elimination of Hydrogen, Chloride from Chlorohydrins. 2. Simulation of the Reaction Unit, Industrial and Engineering Chemistry/Process Design and Development, American Chemical Society, Washington, D.C., U.S. vol. 18, No. 3, Jul. 1, 1979, pp. 428-433, XP008104206, ISSN: 0019-7882.

*Primary Examiner* — Bernard Dentz (57) ABSTRACT

A process and apparatus are disclosed for the purification of epichlorohydrin. The process includes distilling and/or fractionating a feed stream containing epichlorohydrin, dichlorohydrin(s), and one or more other substances, subjecting at least a portion of the liquid phase effluent to a dichlorohydrin dehydrochlorination process for converting residual dichlorohydrin(s) in the liquid phase effluent to epichlorohydrin, and recovering purified epichlorohydrin from the vapor phase effluent in which the distillation/fractionation pressure and/or temperature of step (1) is adjusted to retain at least 5 weight-percent epichlorohydrin in the liquid phase effluent. The apparatus for making purified epichlorohydrin includes a dehydrochlorination apparatus, a first liquid-vapor contacting apparatus, and a second liquid-vapor contacting apparatus connected to the dehydrochlorination apparatus for recycling a distillate to the dehydrochlorination apparatus. Advantages include more efficient recovery of epichlorohydrins and reduced capital investment in recovery equipment.

11 Claims, 1 Drawing Sheet

FIG. 1

PROCESS AND APPARATUS FOR PRODUCING AND PURIFYING EPICHLOROHYDRINS

CROSS REFERENCE TO RELATED APPLICATIONS

This is a §371 application of PCT International Patent Application Number PCT/US2009/031630 filed Jan. 22, 2009, and claims priority from provisional application Ser. No. 61/067,324 filed Feb. 27, 2008 and provisional application Ser. No. 61/031,570 filed Feb. 26, 2008, each of which is incorporated herein by reference in its entirety.

BACKGROUND OF THE INVENTION

The present invention relates to processes and apparatus for recovering and purifying epichlorohydrins from a mixture comprising the same such as the effluent generated by a process for dehydrochlorination of dichlorohydrins.

Epichlorohydrin is a widely used precursor to epoxy resins. Epichlorohydrin is a monomer which is commonly used for the alkylation of para-bisphenol A. The resultant diepoxide, either as a free monomer or oligomeric diepoxide, may be advanced to high molecular weight resins which are used for example in electrical laminates, can coatings, automotive topcoats and clearcoats. Processes and apparatus for making and purifying epichlorohydrin are known in the state of the art.

British Patent Specification 974,164, for example, discloses a process and apparatus for the production of epichlorohydrin from dichlorohydrin in which an aqueous reaction medium comprising an inorganic alkali hydroxide, water and dichlorohydrin are mixed and then treated with steam in a reactor column at a temperature below 55° C. to strip epichlorohydrin formed by the reaction between the inorganic alkali hydroxide and dichlorohydrin from the reaction mixture as a gaseous water-epichlorohydrin azeotrope. The overhead is condensed and separated in a liquid-liquid phase separator into an aqueous phase, which is recycled to the dehydrochlorination reactor column, and an organic phase, which is fed to a drying column to remove epichlorohydrin and residual water as a vapor phase. The vapor phase is condensed and recycled to the liquid-liquid phase separator to remove residual water from the drying column.

The bottoms from the drying column are fed to a finishing column. The vapor phase from the finishing column is condensed to recover epichlorohydrin. The liquid phase effluent from the bottom of finishing column is mixed with water to extract residual unreacted dichlorohydrin for recycle to the dehydrochlorination process.

While that process is capable of producing epichlorohydrin, further improvements in epichlorohydrin yield and purity and lower energy and capital investment requirements for a given production rate and purity are desired. Opportunities remain to further improve the recovery of epichlorohydrins in a form that can be used in subsequent conversions, such as the conversion to epoxy resins.

Accordingly, it is desired to provide improved processes and apparatus for separating the product epichlorohydrin from the dehydrochlorination reaction effluent. These and other problems are solved by the present invention described below.

SUMMARY OF THE INVENTION

A process and apparatus are disclosed for the purification of epichlorohydrin. The process includes (1) distilling and/or fractionating a feed stream containing epichlorohydrin, dichlorohydrin(s), and one or more other substances, (2) subjecting at least a portion of the liquid effluent stream to a dichlorohydrin dehydrochlorination process for converting residual dichlorohydrin(s) in the liquid effluent stream to epichlorohydrin, and (3) recovering purified epichlorohydrin from the vapor phase effluent produced in step (1) in which the distillation/fractionation pressure and/or temperature of step (1) is adjusted to retain at least 5 weight-percent epichlorohydrin in the liquid effluent stream produced by step (1) and/or the distillation/fractionation pressure and/or temperature of step (1) is adjusted to satisfy the equation:

$$R \geq \left[ \frac{100000 \cdot P}{100 \cdot T_K} \right]$$

wherein P represents the distillation pressure of the vapor phase effluent produced by step (1) in Pascal, $T_k$ represents the distillation temperature of the liquid phase effluent produced by step (1) in degrees Kelvin, and R represents the number 2.8. The apparatus for making purified epichlorohydrin includes a dehydrochlorination apparatus, a first liquid-vapor contacting apparatus, and a second liquid-vapor contacting apparatus connected to the dehydrochlorination apparatus for recycling a liquid effluent stream to the dehydrochlorination apparatus. Advantages include more efficient recovery of epichlorohydrins and reduced capital investment in recovery equipment.

A first aspect of the present invention is a process for purifying epichlorohydrin comprising:

(1) distilling and/or fractionating a feed stream comprising epichlorohydrin, dichlorohydrin(s), up to 5 weight-percent of one or more substances other than dichlorohydrin(s) having a boiling point at the distillation and/or fractionation pressure that is higher than the boiling point of epichlorohydrin at the same pressure, and optionally one or more substances other than epichlorohydrin having a boiling point at the distillation and/or fractionation pressure that is lower than or equal to the boiling point of epichlorohydrin at the same pressure, wherein the distillation and/or fractionation is carried out at a pressure below atmospheric pressure and temperature sufficient to separate a vapor phase effluent comprising epichlorohydrin from a liquid phase effluent comprising dichlorohydrin(s), epichlorohydrin, and one or more substances other than epichlorohydrin and dichlorohydrin;

(2) optionally removing one or more substances other than epichlorohydrin and dichlorohydrin from at least a portion of the liquid phase effluent of step (1);

(3) subjecting at least a portion of the liquid phase effluent of step (1) to dichlorohydrin dehydrochlorination for converting the dichlorohydrin(s) of the liquid phase effluent to epichlorohydrin; and (4) recovering the vapor phase effluent of step (1) comprising purified epichlorohydrin, wherein the distillation/fractionation pressure and/or temperature of step (1) is adjusted to retain at least 5 weight-percent epichlorohydrin in the liquid effluent stream produced by step (1) and/or the distillation/fractionation pressure and/or temperature of step (1) is adjusted to satisfy the equation:

$$R \square \left[ \frac{100000 \square P}{1000 \square T_K} \right]$$

wherein P represents the distillation pressure of the vapor phase effluent produced by step (1) in Pascal, $T_k$ represents the distillation temperature of the liquid phase effluent produced by step (1) in degrees Kelvin, and R represents the number 2.8.

A second aspect of the present invention is a process for producing epichlorohydrin comprising:
  (a) contacting a feed stream comprising dichlorohydrin(s) and/or ester(s) thereof and one or more substances other than dichlorohydrin(s) and/or ester(s) thereof with a base in the presence of water under dichlorohydrin dehydrochlorination conditions to produce a dehydrochlorination effluent stream comprising epichlorohydrin, unconverted dichlorohydrin(s), one or more substances other than epichlorohydrin and dichlorohydrin(s) having a boiling point higher than the boiling point of epichlorohydrin and one or more substances other than epichlorohydrin and dichlorohydrin(s) having a boiling point lower than the boiling point of epichlorohydrin;
  (b) distilling and/or fractionating the dehydrochlorination effluent stream of step (a) at a pressure below atmospheric pressure and temperature sufficient to separate a vapor effluent stream comprising epichlorohydrin and one or more substances other than epichlorohydrin having a boiling point lower than or equal to the boiling point of epichlorohydrin from a liquid effluent stream comprising epichlorohydrin, dichlorohydrin(s), and one or more substances other than epichlorohydrin and dichlorohydrin(s); and
  (c) using at least a portion, preferably all or substantially all, of the liquid effluent stream of step (b) as the feed stream in the process according to the first aspect of this invention.

A third aspect of the present invention is an apparatus suitable for producing epichlorohydrin from dichlorohydrin(s) comprising:
  (1) a dehydrochlorination apparatus (100) for conducting dichlorohydrin(s) dehydrochlorination comprising one or more reactor vessels (110), at least one feed stream inlet (111), at least one steam inlet (113) for connection to a steam source, at least one dehydrochlorination product effluent outlet (112), and optionally one or more steam stripping columns connected between the one or more reactors and the at least one dehydrochlorination product effluent outlet;
  (2) a first liquid-vapor contacting apparatus (200) for distilling a mixture comprising epichlorohydrin, dichlorohydrin(s), one or more substances other than dichlorohydrin(s) having a boiling point higher than epichlorohydrin and one or more substances other than epichlorohydrin having a boiling point lower than or equal to epichlorohydrin comprising a liquid-vapor contacting device (210), a heating or evaporating apparatus (220) for heating or evaporating a liquid in the lower portion of the liquid-vapor contacting device and a cooling apparatus (230) for condensing epichlorohydrin and one or more substances having a boiling point lower than epichlorohydrin, the liquid-vapor contacting device (210) having an upper portion (211), a lower portion (212), a vapor phase effluent outlet (213) in the upper portion, a liquid phase effluent outlet (214) in the lower portion, and at least one feed stream inlet (215) between the vapor phase effluent outlet and the liquid phase effluent outlet and the cooling apparatus (230) comprising one or more cooling devices and, optionally, one or more vapor purges; and
  (3) a second liquid-vapor contacting apparatus (300) for distilling a mixture comprising epichlorohydrin, dichlorohydrin(s), one or more substances other than dichlorohydrin(s) having a boiling point higher than epichlorohydrin and optionally one or more substances other than epichlorohydrin having a boiling point lower than or equal to epichlorohydrin comprising a liquid-vapor contacting device (310), a heating or evaporating apparatus (320) for heating or evaporating a liquid in the lower portion of the liquid-vapor contacting device and a cooling apparatus (330) for condensing epichlorohydrin, the liquid-vapor contacting device (310) comprising an upper portion (311), a lower portion (312), a vapor phase effluent outlet (313) in the upper portion, a liquid phase effluent outlet (314) in the lower portion, and at least one feed stream inlet (315) between the vapor phase effluent outlet and the liquid phase effluent outlet and the cooling apparatus (330) comprising one or more cooling devices and, optionally one or more vapor purges;

wherein the dehydrochlorination product effluent outlet of the dehydrochlorination apparatus (100) is connected to the feed stream inlet of the liquid-vapor contacting device (2101) of the first liquid-vapor contacting apparatus (200) by a passage suitable for conducting dichlorohydrin dehydrochlorination reactor (110) effluent from the dichlorohydrin dehydrochlorination apparatus (100) to the liquid-vapor contacting device (210) of the first liquid-vapor contacting apparatus (200);

the liquid phase effluent outlet of the first liquid-vapor contacting apparatus (200) is connected to the feed stream inlet (315) of the liquid-vapor contacting device (310) of the second liquid-vapor contacting apparatus (300) by a passage suitable for conducting liquid phase effluent from the liquid-vapor contacting device (210) of the first liquid-vapor contacting apparatus (200) to the liquid-vapor contacting device (310) of the second liquid-vapor contacting apparatus (300); and the liquid phase effluent outlet (322) of the liquid-vapor contacting device (310) of the second liquid-vapor contacting apparatus (300) is connected to one or more reactor(s) (110) of the dichlorohydrin dehydrochlorination apparatus (100) by a passage suitable for conducting a liquid phase effluent from the liquid-vapor contacting device (310) of the second liquid-vapor contacting apparatus (300) to the one or more reactor(s) (110) of the dichlorohydrin dehydrochlorination apparatus (100).

DETAILED DESCRIPTION OF THE INVENTION

Definitions

As used herein, the term "epichlorohydrin" refers to the compound 1-chloro-2,3-epoxypropane (referred to hereafter by the abbreviation "ECH").

As used herein, the term "dichlorohydrin" means chlorohydrin having two chlorine atoms and at least one hydroxyl group, wherein at least one chlorine atom and at least one hydroxyl group are covalently bonded to two separate vicinal aliphatic carbon atoms (referred to hereafter by the abbreviation "DCH"). DCHs include 1,3-dichloro-2-propanol and 2,3-dichloro-1-propanol.

As used herein, the expression "under dehydrochlorination conditions" means conditions capable of converting at least about 10 weight-percent, preferably at least about 50 weight-percent, more preferably at least about 90 weight-percent of DCHs present in a mixture and/or feed stream into ECH.

As used herein, the term "impurities" means compound(s) other than ECH, DCH(s), and water. Impurities can be byproducts produced in the dehydrochlorination step or in any upstream unit operations use to produce DCH. Impurities can also be substances fed into any unit operation upstream of a unit operation according to the present invention, such as the dehydrochlorination process or the process to produce DCH, which have not been converted into DCH(s) and/or ECH. Examples of byproducts include acrolein (referred to hereafter by the abbreviation "ACRO"), 2-chloroallyl alcohol (referred to hereafter by the abbreviation "BCAA"), 1,2,3-trichloropropane (referred to hereafter by the abbreviation "TCP"), dichloropropoxypropane (referred to hereafter by the abbreviation "DCOPP"), acetaldehyde, methanol, acetone, allyl chloride, allyl alcohol, 2,3-butandione, 2-butanone, 1,2-dichloroethane, 1,4-dioxane, monochloroacetone, glycidol, monochlorobenzene, chloroaliphatic alcohols, chloroaliphatic ethers, fatty acids and carboxylic acids.

As used herein, the expression, "liquid-phase" refers to a continuous intermediate phase between gas phase and a solid phase that may optionally comprise a minor amount of gas and/or solid discrete phase(s). The liquid phase may comprise one or more immiscible liquid phases and may contain one or more dissolved gases, liquids, or solids. Unless specified otherwise, the expression, "liquid-phase effluent" when used in reference to a distillation and/or fractionation step or a liquid-vapor contacting apparatus refers to a distillate produced by the referenced distillation and/or fractionation process or a liquid-vapor contacting apparatus.

As used herein, the expression "vapor phase" refers to a continuous gaseous phase that may optionally comprise a minor amount of liquid and/or solid discrete phase(s) (e.g., aerosol). The vapor phase may be a single gas or a mixture, such as a mixture of two or more gases or two or more liquid discrete phases. Unless specified otherwise, the expression, "vapor-phase effluent" when used in reference to a distillation and/or fractionation step or a liquid-vapor contacting apparatus refers to substances in the vapor phase produced by the referenced distillation and/or fractionation step or liquid-vapor contacting apparatus.

As used herein, the expression "liquid-vapor contacting device" refers to devices that serve to provide the contacting and development of at least one interfacial surface between liquid and vapor in the device. Examples of liquid-vapor contacting devices include plate column, packed column, wetted-wall (falling film) column, spray chamber, heat exchanger or any combination thereof. Examples of devices comprising plate columns and packed columns include distillation columns, fractionation columns, and stripping columns.

As used herein, the term "light boiling" refers to one or more substances having a boiling point less than or equal to the boiling point of epichlorohydrin.

As used herein, the term "heavy boiling" refers to one or more substances having a boiling point higher than the boiling point of epichlorohydrin.

As used herein, the expression "liquid-liquid phase separation device" refers to a device capable of separating a feed stream comprising aqueous and organic components into a predominantly aqueous effluent stream and a predominantly organic effluent stream. The liquid-liquid phase separation device is preferably a device capable of separating fluids according to their relative density, such as a decanter.

As used herein, the term "heating device" means a system for providing heat transfer to a process fluid via a secondary fluid used as a heat source. The process fluid and the secondary fluid may be either physically separated or in direct contact. In distillation and/or fractionation, a heating device can be a system that receives a liquid effluent stream from the liquid-vapor contacting device and either partially or completely vaporizes that stream to provide the vapor driving the separation in the liquid-vapor contacting device, such as a reboiler. The heating device may be a unit operation either external or internal to a liquid-vapor contacting device. Examples of heating devices are kettle reboiler, thermosyphon reboiler and forced circulation reboiler. The secondary fluid may be a vapor, a liquid, or a combination of liquid and vapor. Examples of secondary fluid as a heat sources are steam, hot oil and Dowtherm™.

As used herein, the term "cooling device" means a system for providing heat transfer from a process fluid via a secondary fluid used as a coolant. The process fluid and the secondary fluid may be either physically separated or in direct contact. In distillation and/or fractionation, a cooling device can be a system that receives a vapor effluent stream from the liquid-vapor contacting device and either partially or completely condenses that stream by transferring the latent heat from the vapor effluent stream to the coolant, such as a condenser. The cooling device may be a unit operation either external or internal to a liquid-vapor contacting device. Examples of cooling devices are shell and tube typed heat exchanger and air-cooled typed heat exchanger. The secondary fluid may be a vapor, a liquid, or a combination of liquid and vapor. Examples of secondary fluid as a coolant are water and air.

As used herein, the term "multihydroxylated-aliphatic hydrocarbon compound" (abbreviated hereafter as "MAHC") refers to a compound that contains at least two hydroxyl groups covalently bonded to two separate vicinal carbon atoms and no ether linking groups. They contain at least two sp3 hybridized carbons each bearing an OH group. The MAHCs include any vicinal-diol (1,2-diol) or triol (1,2,3-triol) containing hydrocarbon including higher orders of contiguous or vicinal repeat units. The definition of MAHC also includes for example one or more 1,3-1,4-, 1,5- and 1,6-diol functional groups as well. Geminal-diols, for example, are precluded from this class of MAHCs.

The MAHCs contain at least about 2, preferably at least about 3, up to about 60, preferably up to about 20, more preferably up to about 10, even more preferably up to about 4, and yet more preferably up to about 3, carbon atoms and can contain, in addition to aliphatic hydrocarbon, aromatic moieties or heteroatoms including for example halide, sulfur, phosphorus, nitrogen, oxygen, silicon, and boron heteroatoms; and mixtures thereof. The MAHCs may also be a polymer such as polyvinyl alcohol.

The terms "glycerin", "glycerol" and "glycerine", and esters thereof, may be used as synonyms for the compound 1,2,3-trihydroxypropane, and esters thereof.

As used herein, the term "chlorohydrin" means a compound containing at least one hydroxyl group and at least one chlorine atom covalently bonded to two separate vicinal aliphatic carbon atoms and no ether linking groups. Chlorohydrins are obtainable by replacing one or more hydroxyl groups of MAHCs with covalently bonded chlorine atoms via hydrochlorination. The chlorohydrins contain at least about 2, and preferably at least about 3, up to about 60, preferably up to about 20, more preferably up to about 10, even more preferably up to about 4, and yet more preferably up to about 3, carbon atoms and, in addition to aliphatic hydrocarbon, can contain aromatic moieties or heteroatoms including for example halide, sulfur, phosphorus, nitrogen, oxygen, silicon, and boron heteroatoms, and mixtures thereof. A chlorohydrin that contains at least two hydroxyl groups is also a MAHC.

As used herein, the term "monochlorohydrin" means chlorohydrin having one chlorine atom and at least two hydroxyl groups, wherein the chlorine atom and at least one hydroxyl group are covalently bonded to two separate vicinal aliphatic carbon atoms (referred to hereafter by the abbreviation "MCH"). MCH produced by hydrochlorination of glycerin or glycerin esters includes, for example, 3-chloro-1,2-propanediol and 2-chloro-1,3-propanediol.

Unless specified otherwise, the term "weight-percent" refers to the mass flow rate of a specified substance relative to the total mass flow rate of a specified stream containing the specified substance.

Each and every document cited herein is fully incorporated by reference herein for its content to the extent that the content thereof relates to the purpose for which it is cited.

Distillation and/or Fractionation Process

Distillation and/or fractionation is performed at a vapor phase effluent pressure preferably equal to at least about 5, more preferably at least about 10, even more preferably at least about 20, kPa and preferably up to about atmospheric pressure, more preferably up to about 80, and even more preferably up to about 60, kPa. The pressure of distillation and/or fractionation may be measured at the head of the liquid-vapor contacting device used to perform the distillation and/or fractionation.

Distillation and/or fractionation is performed at a liquid phase effluent temperature preferably equal to at least about 80, more preferably at least about 90, even more preferably at least about 100° C., and preferably up to about 150, more preferably up to about 130, even more preferably up to about 120, and yet more preferably up to about 110° C. The temperature of distillation and/or fractionation may be measured at the bottom, or sump, of the liquid-vapor contacting device used to perform the distillation and/or fractionation.

Each distillation and/or fractionation step enriches the concentration of DCH(s) in the liquid phase effluent stream relative to the concentration of DCH(s) that were present in the feed stream prior to the same distillation and/or fractionation step.

The distillation and/or fractionation process is preferably performed as a continuous process and is preferably performed under reflux conditions. A lower boiling effluent stream and a higher-boiling liquid phase effluent stream are drawn off, preferably continuously. Distilling and/or fractionating is preferably carried out in a liquid-vapor contacting device.

First Liquid-Vapor Contacting Step

The feed stream processed in the first liquid-vapor contacting step comprises ECH, DCH(s), and one or more substances other than ECH and DCH. The one or more substances other than ECH and DCH preferably include water and may include one or more impurities. The ECH concentration in that feed stream is preferably at least about 80, more preferably at least about 90, and even more preferably at least about 95, weight-percent and preferably up to about 99 weight-percent.

DCH may be present in amounts up to about 15, more preferably up to about 8, even more preferably up to about 4 weight-percent, and may be present in amounts as low as about 0.5 weight-percent, for example.

The water concentration is preferably up to about 15, more preferably up to about 9, and even more preferably up to about 4, weight-percent, and may be as low as about 1 weight-percent.

ACRO is an impurity that may be present as a lower boiling substance. When ACRO is present, the ACRO concentration in the feed stream is preferably less than about 0.5 weight-percent and more preferably less than about 0.1 weight-percent, and may be as low as about 100 parts per million (ppm), or even as low as about 10 ppm.

BCAA is an impurity that may be present as a higher boiling substance. When BCAA is present, the BCAA concentration in the feed stream is preferably less than about 0.5 weight-percent and more preferably less than about 0.1 weight-percent, and may be as low as about 10 ppm, or even as low as about 1 ppm.

TCP is an impurity that may also be present as a higher boiling substance. When TCP is present, the TCP concentration is preferably less than about 4, more preferably up to about 2, and even more preferably up to about 1, weight-percent, and may be as low as about 300 ppm, or even as low as about 30 ppm.

DCOPP is an impurity that may be present as a higher boiling substance. When DCOPP is present, the DCOPP may be present in an amount up to about 1, more preferably up to about 0.5, weight-percent.

The feed stream is distilled and/or fractionated to separate a vapor-phase effluent comprising at least ECH and components having a boiling point equal to or lower than ECH, such as water and ACRO, from the liquid-phase mixture. The distillation and/or fractionation produces a vapor phase effluent preferably containing at least about 95, more preferably at least about 98, weight-percent of the components of the feed stream having a boiling point lower than the boiling point of ECH that were present in the feed stream prior to distillation and/or fractionation.

After the distillation and/or fractionation unit operation, the vapor-phase effluent is preferably cooled to a temperature below the dew points of ECH and water, and preferably above the dew point of substances having a boiling point lower than the boiling point of water, such as ACRO, at the pressure of the vapor phase effluent stream undergoing cooling to form a condensed liquid-phase effluent stream comprising ECH and water. Cooling is preferably carried out using a cooling device, such as a condenser.

The condensed vapor-phase effluent stream obtained from the first liquid-vapor contacting apparatus is preferably separated into an aqueous fraction and an organic fraction via liquid-liquid phase separation. The organic fraction of the condensed liquid-phase effluent stream is preferably recycled to the liquid-vapor contacting device of the first liquid-vapor contacting apparatus to provide additional liquid for reflux during distillation or fractionation. The aqueous fraction, which generally contains a certain concentration of ECH, is preferably recycled to recover the saturated ECH present in the aqueous fraction and recycle water. The aqueous fraction is preferably recycled to a dehydrochlorination process, especially to a dehydrochlorination process providing the feed stream to the first liquid-vapor contacting step. Liquid-liquid phase separation is preferably carried out using a decanter.

Second Liquid-Vapor Contacting Step

The feed stream processed in the second liquid-vapor contacting step comprises ECH, DCH(s) and, optionally, one or more substances other than ECH and DCH. The one or more substances other than ECH and DCH may include one or more higher boiling substances, including higher boiling impurities, and optionally, lower boiling substances, such as one or more lower boiling impurities.

The ECH concentration in that feed stream is preferably at least about 80, more preferably at least about 90, and even more preferably at least about 95, weight-percent and preferably up to about 99 weight-percent.

DCH may be present in amounts up to about 15, more preferably up to about 8, even more preferably up to about 4, weight-percent, and may be present in amounts as low as about 0.5 weight-percent, for example.

The concentration of substances having a boiling point lower than the boiling point of ECH, such as water, is preferably less than about 0.5, more preferably less than about 0.1, even more preferably less than about 0.05, and yet more preferably less than about 0.01, weight-percent.

Impurities include, inter alia, higher boiling impurities such as BCAA, TCP, and DCOPP. BCAA, TCP, and DCOPP may be present at concentrations within the ranges described above in reference to the feed stream of the first liquid-vapor contacting step.

The feed stream for the second liquid-vapor contacting step preferably comprises the liquid phase effluent stream from the first liquid-vapor contacting stream described above. Since light boiling impurities such as ACRO are substantially removed by distillation/fractionation from the feed stream introduced into the first liquid-vapor contacting step, the liquid phase effluent stream from the first liquid-vapor contacting step preferably contains less than about 100 ppm, more preferably less than about 10 ppm, light boiling impurities.

The feed stream is distilled or fractionated to separate a vapor-phase effluent comprising at least ECH from the liquid-phase mixture. The vapor phase effluent preferably contains less than about 100 ppm unreacted DCH and less than about 500 ppm impurities.

The vapor-phase effluent is preferably cooled to a temperature below the dew point of ECH at the pressure of the vapor phase effluent stream undergoing cooling to form a condensed liquid-phase effluent stream comprising at least ECH. Cooling is preferably carried out using a cooling device, such as a condenser.

To reduce the capital investment and energy costs associated with the cooling step, condensation of the vapor-phase effluent is preferably carried out at a temperature at which refrigerated cooling is not required. In particular, the cooling step is preferably carried out at a pressure such that the condensation temperature is at least about 20° C., and more preferably at least about 30° C.

The distillation/fractionation pressure and/or temperature of the second liquid-vapor contacting step is preferably adjusted to satisfy the equation:

$$R \square \left[ \frac{100000 \square P}{100 \square T_K} \right]$$

wherein P represents the distillation pressure of the vapor phase effluent produced by step (1) in Pascal, $T_k$ represents the distillation temperature of the liquid phase effluent produced by step (1) in degrees Kelvin, and R represents the number 2.8, preferably 3.1, more preferably 3.2, and even more preferably 3.3.

A portion of the condensed vapor effluent stream is preferably recycled to the liquid-vapor contacting device of the second liquid-vapor contacting apparatus to provide additional reflux for the liquid-vapor contacting device. The condensed vapor effluent stream may contain less than about 0.2, more preferably less than about 0.1, and even more preferably less than about 0.05, weight-percent impurities.

At least a fraction, preferably at least about 80, more preferably at least about 90, weight-percent of the liquid-phase effluent produced by the second liquid-vapor contacting step is recycled to the dehydrochlorination process. The liquid phase effluent stream produced by the second liquid-vapor contacting step preferably comprises unreacted DCH, ECH, and optionally one or more substances other than DCH and ECH (primarily higher boiling substances such as higher boiling impurities).

DCH may be present in this recycle stream in amounts up to about 90, more preferably up to about 80, even more preferably up to about 70, weight-percent, and may be present in amounts as low as about 20 weight-percent, for example.

ECH is present in this recycle stream at a concentration of at least 5 about, preferably at least about 10, more preferably at least about 20, and yet more preferably at least about 30, weight-percent and preferably up to about 50, even more preferably up to about 40, weight-percent.

Impurities include, inter alia, BCAA, TCP, and DCOPP. BCAA may be present in an amount up to about 3 weight-percent, more preferably up to about 1 weight-percent. TCP may be present in an amount up to about 20, more preferably up to about 15, and even more preferably up to about 10, weight-percent and as low as about 1 weight-percent. DCOPP may be present in an amount up to about 5, more preferably up to about 1, weight-percent. Byproducts, particularly heavy byproducts, may be removed by purging them from the process, such as by purging them from the liquid-phase effluent produced by the second liquid-vapor contacting step.

The liquid phase effluent stream subjected to dichlorohydrin dehydrochlorination preferably contains less than about 1, more preferably less than about 0.1, and even more preferably less than about 0.01, weight-percent lighter boiling substances. In particular, that liquid phase effluent stream preferably contains less than about 1, more preferably less than about 0.1, and even more preferably less than about 0.01, weight-percent water.

The liquid phase effluent stream subjected to the dichlorohydrin dehydrochlorination process preferably comprises DCH at a concentration preferably up to about 90, more preferably up to about 80, even more preferably up to about 70, weight-percent, and as low as about 20 weight-percent, for example. The DCH concentration leaving the last distillation step is preferably substantially the same as the DCH concentration subjected to a dichlorohydrin dehydrochlorination process.

The liquid phase effluent subjected to a dichlorohydrin dehydrochlorination process preferably comprises ECH at a concentration of at least about 5, preferably at least about 10, more preferably at least about 20, and yet more preferably at least about 30, weight-percent and preferably up to about 50, even more preferably up to about 40, weight-percent. The ECH concentration leaving the last distillation step is preferably substantially the same as the ECH concentration subjected to a dichlorohydrin dehydrochlorination process.

The liquid phase effluent stream is preferably recycled to the dichlorohydrin dehydrochlorination process that produces at least a portion, preferably all, of the ECH in the feed stream to this distillation step. The recycle stream from the second liquid-vapor contacting step to the dehydrochlorination step is preferably recycled without subjecting the recycle stream to a unit operation for separating the stream into a stream enriched in DCH and a stream impoverished of DCH, and/or for separating the stream into a stream enriched in ECH and a stream impoverished of ECH, prior to the dichlorohydrin dehydrochlorination step. The recycle stream is preferably not subjected to a water extraction step, an organic solvent extraction step or an additional distillation step.

Dehydrochlorination Process

Dehydrochlorination may be carried out by contacting one or more effluent streams comprising DCH(s) with an inorganic base. The inorganic base is not particularly limited. For example, an aqueous solution or suspension of calcium hydroxide, sodium hydroxide, potassium hydroxide, sodium carbonate, potassium carbonate or the like may be used, however, the present invention is not limited thereto. Preferred inorganic base include alkali metal hydroxides and alkaline earth metal hydroxides. The alkali metal is preferably the sodium cation, $Na^+$ and the alkaline earth metal is preferably calcium cation, $Ca^{+2}$.

The amount of the inorganic base used is not particularly limited. The amount of the alkaline compound used is preferably from about 1.0 to about 1.5 equivalent, more preferably from about 1.01 to about 1.3 equivalent, per mol of DCH and/or esters thereof and any neutralizable chlorinating agent that may be present.

The reaction between dichlorohydrin(s) and the inorganic base forms epichlorohydrin and one or more chloride salts comprising the inorganic base cation(s). In the case of the preferred inorganic bases, the chloride salt may be an alkali metal chloride, such as sodium chloride, or alkaline earth metal chloride, such as calcium chloride.

The production of ECH may be performed by any known process. For example, similarly to the methods described in U.S. Pat. No. 4,952,647, British Patent No. 974,164 and Japanese Unexamined Patent Publication (Kokai) No. 60-258172, a method of reacting dichloropropanol with an aqueous alkali solution or suspension and thereby producing ECH may be preferably used. However, the process is not limited thereto.

Preferred examples of the dichlorohydrin dehydrochlorination process include:
(1) a method of supplying DCH and/or esters thereof as the starting material and an aqueous alkali solution or suspension from the top of a plate distillation column, blowing steam from the bottom, and stripping ECH produced by the reaction while causing azeotropic distillation with water; in this method, the stripping effect may be increased by allowing an inert gas such as nitrogen to accompany the steam;
(2) a method of mixing DCH and/or esters thereof or an aqueous solution with an aqueous alkali solution or suspension in a liquid phase and reacting them while stirring; and
(3) a method of allowing the reaction to proceed in the presence of an inactive solvent substantially insoluble in water while extracting ECH in the solvent.

In the methods (2) and (3), the reaction may be performed either batchwise or continuously. In the case of continuous reaction, a mixing tank-type reaction or a flow-type reaction in a tower reactor or the like may be used. In the case of a flow-type reaction in a tower reactor, DCH and/or esters thereof or a solution thereof and an aqueous alkali solution or suspension may flow cocurrently or countercurrently while coming into contact, to thereby effect reaction. The reaction methods (2) and (3) may be combined, for example, so that the reaction is performed by one method to a certain degree and the reaction is further allowed to proceed according to the other method.

The amount of steam used for the stripping of ECH produced in the second step may suitable be such that the top distillate composition has a water/ECH ratio by weight of from about 0.5 to about 3.5, and preferably from about 1.0 to about 2.5. As the amount of steam becomes larger, the selectivity of ECH increases. However, if the steam amount is too large, the steam yield may decrease so that the amount used is limited in practice, whereas if the steam amount is too small, the stripping effect may be reduced and the selectivity of ECH may decrease.

The dehydrochlorination reaction temperature is not particularly limited but it is preferably at least about 10° C., more preferably at least about 30° C., and even more preferably at least about 60° C., preferably up to about 110° C., more preferably up to about 100° C., even more preferably up to about 90° C.; and yet more preferably up to about 80° C. As the reaction temperature becomes lower, the selectivity of ECH increases, however, the reaction rate may decrease and the reaction time may be prolonged.

The reaction pressure is not particularly limited but it is preferably from about 10 to about 200 kPa. The dehydrochlorination reaction can be conducted at pressures suitably from about 1 to about 100 kPa, more suitably from about 10 to about 80 kPa, and most suitably from about 15 to about 40 kPa.

The dehydrochlorination reaction can be conducted in the presence of such solvents as alcohols, aromatic hydrocarbons, aliphatic ethers, aromatic ethers, polyethers, ketones, chlorobenzenes, chlorinated epoxides, any combination thereof and the like. Particularly suitable solvents include, for example, methanol, ethanol, n-propanol, isopropanol, n-butanol, toluene, benzene, xylene, methyl isobutyl ketone, 2-ethoxy-1-propanol, dimethoxy ethane, dimethoxypropane, trimethoxypropane, dichlorobenzenes, methylene chloride, acetone, methyl ethyl ketone, ECH, any combination thereof and the like.

The feed stream introduced into the dehydrochlorination step may be obtained directly or indirectly from any process for making DCHs and/or esters thereof. Preferred processes for providing the desired feed stream compositions for this process include processes for converting allyl chloride, allyl alcohol, and/or MAHC(s) into DCHs and/or esters thereof.

Processes for converting MAHC(s) such as glycerin to DCH via hydrochlorination are particularly preferred. For example, German Patent No. 197308 teaches a process for preparing a chlorohydrin by the catalytic hydrochlorination of glycerin by means of anhydrous hydrogen chloride. WO 2005/021476 discloses a continuous process for preparing the dichloropropanols by hydrochlorination of glycerin and/or monochloropropanediols with gaseous hydrogen chloride with catalysis of a carboxylic acid. WO 2006/020234 A1 describes a process for conversion of a glycerol or an ester or a mixture thereof to a chlorohydrin, comprising the step of contacting a MAHC, an ester of a MAHC, or a mixture thereof with a source of a superatmospheric partial pressure of hydrogen chloride to produce a chlorohydrin, an ester of a chlorohydrin, or a mixture thereof in the presence of an organic acid catalyst without substantially removing water. The above references are hereby incorporated herein by reference with respect to the above-described disclosures.

In an exemplifying MAHC hydrochlorination process, MAHC and a hydrochlorination catalyst are charged to the hydrochlorination reactor. Then a chlorinating agent such as hydrogen chloride is added to the reactor. The reactor pressure is adjusted to the desired pressure and the reactor contents are heated to the desired temperature for the desired length of time. After completion of the hydrochlorination reaction or while carrying out the hydrochlorination reaction, the reactor contents as a reaction effluent stream is discharged from the reactor and fed directly, or indirectly via another reactor or other intervening step, to a separation system comprising a DCH recovery system according to the present invention and optionally including other separation systems or equipment, such as a flash vessel and/or reboiler.

The MAHC hydrochlorination reaction above may be carried out in one or more hydrochlorination reactor vessels such as a single or multiple continuous stirred tank reactors (referred to hereafter by the abbreviation "CSTR"), single or multiple tubular reactor(s), plug flow reactors (referred to hereafter by the abbreviation "PFR"), or combinations thereof. The hydrochlorination reactor can be, for example, one reactor or multiple reactors connected with each other in series or in parallel including, for example, one or more CSTRs, one or more tubular reactors, one or more PFRs, one or more bubble column reactors, and combinations thereof.

In a preferred embodiment, part or all of the hydrochlorination effluent stream is a feed stream from a PFR. A PFR is a type of reactor that has a high length/diameter (L/D) ratio and has a composition profile along the length of the reactor. The concentration of the reactants being fed into the PFR decreases from inlet to the outlet along the flow path of the PFR and the concentration of DCHs increases from inlet to the outlet along the flow path of the PFR. In the case of hydrochlorination of glycerol, the concentration of HCl and glycerol decreases from inlet of the PFR to outlet of the PFR while the total concentration of 1,3-dichloro-2-propanol and 2,3-dichloro-1-propanol increases from inlet of the PFR to the outlet of the PFR.

The equipment useful for conducting the hydrochlorination reaction may be any well-known equipment in the art and should be capable of containing the reaction mixture at the conditions of the hydrochlorination. Suitable equipment may be fabricated of materials which are resistant to corrosion by the process components, and may include for example, metals such as tantalum, suitable metallic alloys (particularly nickel-molybdenum alloys such as Hastalloy C®), or glass-lined equipment, for example.

In addition to DCH(s), one or more of the unreacted MAHC(s) and/or chlorination agent(s), reaction intermediates such as MCH(s), MCH ester(s), and/or DCH ester(s), catalyst(s), ester(s) of catalyst(s), water, and/or impurities may present in MAHC hydrochlorination effluent stream.

Undesirable impurities and/or reaction byproducts are produced during the hydrochlorination process that are not entirely removed by purging them from the hydrochlorination process or post-treatment.

Chlorinating agent that may optionally be present in the dehydrochlorination feed stream is preferably hydrogen chloride dissolved in the dehydrochlorination feed stream. Neutralization of the hydrogen chloride by the base fed to the hydrochlorination process to form a salt and water requires feeding additional base to the dehydrochlorination apparatus.

The DCHs generally correspond to the hydrochlorinated MAHCs in which two hydroxyl groups covalently bonded to two separate carbon atoms, at least one of which is vicinal to a third carbon atom having a hydroxyl group, are each replaced by a covalently bonded chlorine atom. The ester(s) of DCH(s) may be the result of hydrochlorination of MAHC ester(s), MCH ester(s) or reaction(s) with acid catalyst(s), for example.

Carboxylic acids, RCOOH, catalyze the hydrochlorination of MAHCs to chlorohydrins. The specific carboxylic acid catalyst chosen may be based upon a number of factors including for example, its efficacy as a catalyst, its cost, its stability to reaction conditions, and its physical properties. The particular process, and process scheme in which the catalyst is to be employed may also be a factor in selecting the particular catalyst. The "R" groups of the carboxylic acid may be independently chosen from hydrogen or hydrocarbyl groups, including alkyl, aryl, aralkyl, and alkaryl. The hydrocarbyl groups may be linear, branched or cyclic, and may be substituted or un-substituted. Permissible substituents include any functional group that does not detrimentally interfere with the performance of the catalyst, and may include heteroatoms. Non-limiting examples of permissible functional groups include chloride, bromide, iodide, hydroxyl, phenol, ether, amide, primary amine, secondary amine, tertiary amine, quaternary ammonium, sulfonate, sulfonic acid, phosphonate, and phosphonic acid.

Apparatus

The above process may be conducted using an apparatus according to the present invention. The apparatus is now described in more detail in reference to FIG. 1.

Dehydrochlorination Apparatus

Figure 1:
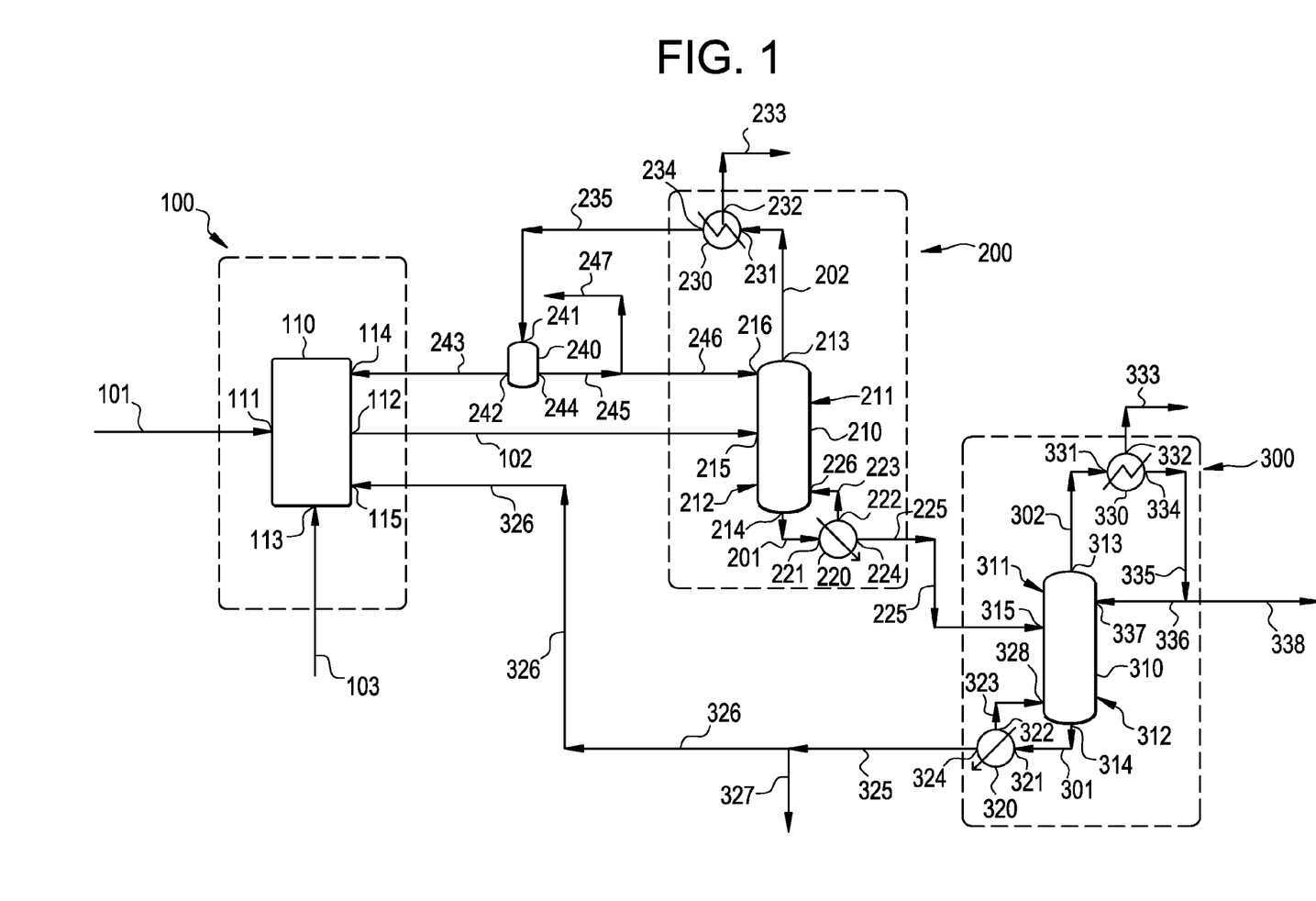
FIG. 1 is a process diagram illustrating an embodiment of the present invention.

With reference to FIG. 1, the apparatus comprises at least one dichlorohydrin dehydrochlorination apparatus generally indicated by numeral (100) comprising one or more dehydrochlorination reactors (110) and optionally one or more stripping columns (not shown). At least one dehydrochlorination reactor (110) is preferably connected directly or indirectly to at least one source of stripping agent for introducing one or more stripping agents, preferably steam, into the bottom of the reactor (110).

The at least one reactor (110) has at least one feed stream inlet (111) for introducing a fresh feed stream (101) comprising DCH and/or esters thereof, at least one reactor effluent outlet (112) connected directly or indirectly via passage (102) to a feed stream inlet (215) of a liquid-vapor contacting device (210) in a liquid-vapor contacting apparatus generally indicated by numeral (200) for distillation and/or fractionation. The at least one reactor (110) may also have a steam inlet (113) connectable to a source of steam for introducing a steam stream (103) for stripping ECH from a reaction mixture in the reactor(s)

First Liquid-Vapor Contacting Apparatus

The first liquid-vapor contacting apparatus generally indicated by numeral (200) comprises a liquid-vapor contacting device (210) comprising an upper portion generally indicated by numeral (211), a lower portion generally indicated by numeral (212), a vapor phase effluent outlet (213) in the upper portion (211), a liquid phase effluent outlet (214) in the lower portion (212), and at least one feed stream inlet (215) between the vapor phase effluent outlet (213) and the liquid phase effluent outlet (214).

The first liquid-vapor contacting apparatus (200) further comprises a heating or evaporating device, such as a reboiler (220), for heating or evaporating a liquid stream (201) exiting from the lower portion (212) of the liquid-vapor contacting device (200) via the liquid phase effluent outlet (214); and a first cooling apparatus comprising at least one cooling device, such as a condenser (230), for cooling a vapor stream (202) exiting from the upper portion (211) of the liquid-vapor contacting device (210) via the vapor phase effluent outlet (213).

The liquid-vapor contacting device (210) has a bottom end (212) and a top end (211) for applying a gradually decreasing temperature gradient from the bottom end to the top end to substances within the liquid-vapor contacting device (210). The liquid-vapor contacting device (210) is preferably a distillation or fractionation column, such as a packed distillation column and/or a distillation column adapted for carrying out fractional distillation under reflux conditions having a reflux zone for carrying out reflux.

The liquid-vapor contacting device (210) is preferably a distillation or fractionation column preferably having at least about 8, more preferably at least about 12, and even more preferably at least about 15, theoretical plates, but may be conducted via a distillation or fractionation column having up to about 20, up to about 25, or even up to about 30, theoretical plates. The column is preferably a plate column, such as perforated-plate column, a tray column, a bubble-cap plate column and/or a packed column.

The liquid-vapor contacting device (210) comprises at least one feed stream inlet (215) at a point intermediate between the bottom (212) and the top (211) of the liquid-vapor contacting device (210), a vapor phase effluent stream outlet (213) to withdraw a lower-boiling stream (202) above the feed stream at or near the top (211) of the liquid-vapor contacting device (210); and at least one liquid phase effluent stream outlet (214) to withdraw a higher-boiling stream (201) at or near the bottom (212) of the liquid-vapor contacting device (210) and preferably below the feed stream inlet (215).

The feed stream (102) from the reactor (110) is preferably fed into the liquid-vapor contacting device (210) via a feed stream inlet (215) below the vapor phase effluent outlet (213) and above the liquid phase effluent outlet (214) as shown. The preferred minimum distance of the feed stream (102) above the evaporation or heating device (220) (the evaporation or heating area or the evaporation zone) depends, inter alia., on the total length of the liquid-vapor separation device (210), the filling with certain packings and/or the minimum spacing of the perforated plates and is, for example, in the case of very long columns or heavily or densely packed columns and the like, greater than one-tenth of the total length of the column. It is, however, particularly expedient for this minimum distance to be greater than about one-eighth or about one-sixth, preferably greater than about one-fifth, more preferably greater than about one-quarter, of the total length of the liquid-vapor contacting device (210).

According to a preferred embodiment, a distance is maintained between the feed stream inlet(s) (215) and the vapor phase effluent outlet(s) (213) which is greater than about one-fifth of the length of the column, preferably greater than about one-quarter of the length of the liquid-vapor contacting device (210).

The liquid phase effluent stream outlet (214) of the liquid-vapor contacting device (210) of the first liquid-vapor contacting apparatus (200) is preferably connected to a liquid phase effluent inlet (221) of reboiler device (220) by a passage (201) suitable for conducting a liquid phase effluent stream (201) from the first liquid-vapor contacting device (210) to the reboiler device (220). Reboiler device (220) preferably has a liquid phase outlet (222) for recycling liquid phase components entering reboiler device (220) back to the liquid-vapor contacting device (210) via liquid recycle stream (223) through an inlet (226) of the liquid-vapor contacting device (210).

A liquid phase effluent stream outlet (224) of reboiler device (220) is connected to the liquid phase effluent stream inlet (315) of the liquid-vapor contacting device (310). The connection may be via a passage (225) suitable for conducting a liquid phase effluent stream (225) from the reboiler device (220) to the liquid-vapor contracting device (310).

The vapor phase effluent outlet (213) of the liquid-vapor contacting device (210) of the first liquid-vapor contacting apparatus (200) is preferably connected to a vapor phase effluent inlet (231) of cooling device (230) by a passage (202) suitable for conducting a vapor phase effluent stream (202) from the first liquid-vapor contacting device (210) to the cooling device (230). Cooling device (230) preferably has a vapor phase outlet (232) for removing vapor phase components entering cooling device (230) which are not condensed by the cooling device (230) via a noncondensed phase passage (233). The cooling device (230) is preferably a nonrefrigerated condenser.

A condensed liquid phase effluent stream outlet (234) of cooling device (230) is connected to a liquid phase effluent stream inlet (241) of a liquid-liquid phase separation device (240). The connection may be via a passage (235) suitable for conducting a condensed liquid phase effluent stream (235) from the cooling device (230) to the liquid-liquid phase separation device (240); or preferably by locating the cooling device (230) above the liquid-liquid phase separation device (240); so that a liquid phase condensed by the cooling device (230) flows into the liquid-liquid phase separation device (240) via gravity flow.

An aqueous liquid phase effluent stream outlet (242) of the liquid-liquid phase separation device (240) is connected, preferably via recycle inlet (114), to one or more reactor(s) (110) of the dichlorohydrin dehydrochlorination apparatus (100) by a passage (243) suitable for conducting an aqueous liquid phase effluent stream (243) from the liquid-liquid phase separation device (240) to one or more of the reactor(s) (110). Although not shown, the recycle inlet (114) may be connected to the feed stream inlet (101) for combining the recycle stream (243) with the fresh feed stream (101) for introducing a combined recycle stream (243) and fresh feed stream into the dichlorohydrin dehydrochlorination apparatus (100).

An organic liquid phase effluent stream outlet (244) of the liquid-liquid phase separation device (240) is connected to an inlet (216) of the top portion (211) of the liquid-vapor contacting device (210) by a passage (245, 246) suitable for conducting an organic liquid-phase effluent stream (245, 246) from the liquid-liquid phase separation device (240) to the top portion (211) of the first liquid-vapor contacting device (210). Impurities may be removed via a purge line (247) from the stream (245, 246) flowing from the liquid-liquid phase separator (240) to the liquid-vapor contacting device (210).

Second Liquid-Vapor Contacting Apparatus

The second liquid-vapor contacting apparatus generally indicated by numeral (300) comprises a liquid-vapor contacting device (310) comprising an upper portion generally indicated by numeral (311), a lower portion generally indicated by numeral (312), a vapor phase effluent outlet (313) in the upper portion (311), a liquid phase effluent outlet (314) in the lower portion (312), and at least one feed stream inlet (315) between the vapor phase effluent outlet (313) and the liquid phase effluent outlet (314).

The second liquid-vapor contacting apparatus (300) further comprises a heating or evaporating device, such as a reboiler (320), for heating or evaporating a liquid stream (301) exiting from the lower portion (312) of the liquid-vapor contacting device (310) via the liquid phase effluent outlet (314); and a cooling device, such as a condenser (330), for cooling a vapor stream (302) exiting from the upper portion (311) of the liquid-vapor contacting device (310) via the vapor phase effluent outlet (313).

The liquid-vapor contacting device (310) has a bottom end (312) and a top end (311) for applying a gradually decreasing temperature gradient from the bottom end to the top end to substances within the liquid-vapor contacting device (310). The liquid-vapor contacting device (310) is preferably a distillation or fractionation column, such as a packed distillation column and/or a distillation column adapted for carrying out fractional distillation under reflux conditions having a reflux zone for carrying out reflux.

The liquid-vapor contacting device (310) is preferably a distillation or fractionation column preferably having at least about 8, more preferably at least about 12, and even more preferably at least about 15, theoretical plates, but may be conducted via a distillation or fractionation column having up to about 20, up to about 25, or even up to about 30, theoretical plates. The column is preferably a plate column, such as perforated-plate column, a tray column, a bubble-cap plate column and/or a packed column.

The liquid-vapor contacting device (310) comprises at least one feed stream inlet (315) at a point intermediate between the bottom (312) and the top (311) of the liquid-vapor contacting device (310); a vapor phase effluent stream outlet (313) to withdraw a lower-boiling stream (302) above the feed stream inlet (315) at or near the top (311) of the liquid-vapor contacting device (310); and at least one liquid phase effluent stream outlet (314) to withdraw a higher-boiling stream (301) at or near the bottom (312) of the liquid-vapor contacting device (310), and preferably below the feed stream inlet (315).

The feed stream (225) from the reboiler (220) is preferably fed into the liquid-vapor contacting device (310) via fed stream inlet (315) below the vapor phase effluent outlet (313) and above the liquid phase effluent outlet (314) as shown. The preferred minimum distance of the feed stream (225) above the evaporation or heating device (320) (the evaporation or heating area or the evaporation zone) depends, inter alia., on the total length of the liquid-vapor separation device (310), the filling with certain packings and/or the minimum spacing of the perforated plates and is, for example, in the case of very long columns or heavily or densely packed columns and the like, greater than about one-tenth of the total length of the column. It is, however, particularly expedient for this minimum distance to be greater than about one-eighth or about one-sixth, preferably greater than about one-fifth, more preferably greater than about one-quarter, of the total length of the liquid-vapor contacting device (310).

According to a preferred embodiment, a distance is maintained between the feed stream inlet(s) (315) and the vapor phase effluent outlet(s) (313) which is greater than about one-fifth of the length of the column, preferably greater than about one-quarter of the length of the liquid-vapor contacting device (310).

The vapor phase effluent outlet (313) of the liquid-vapor contacting device (310) of the second liquid-vapor contacting apparatus (300) is preferably connected to a vapor phase effluent inlet (331) of the cooling device (330) by a passage (302) suitable for conducting a vapor phase effluent stream (302) from the second liquid-vapor contacting device (310) to the cooling device (330). Cooling device (330) preferably has a vapor phase outlet (332) for removing vapor phase components entering the cooling device (330) which are not condensed by the cooling device (330) via a noncondensed phase passage (333).

A condensed liquid phase outlet (334) of the cooling device (330) is connected to a liquid phase inlet (337) of the upper portion (311) of the liquid-vapor contacting device (310) for recycling a portion of a condensed liquid phase (335, 336) from the outlet (334) of the cooling device (330) to the upper portion (311) of the liquid-vapor contacting device (310) via a recycle stream (335, 336) as reflux for the liquid-vapor contacting device (310). The cooling device (330) may be located above, or integral with, the upper portion (311) of the liquid-vapor contacting device (310) to allow a condensed phase to flow from the cooling device (330) into the liquid-vapor contacting device (310) via gravity flow. The cooling device (330) is preferably a nonrefrigerated condenser.

A purified epichlorohydrin product fraction is removed from the recycle stream (335, 336) via product stream passage (338).

The liquid-phase effluent outlet (314) of the liquid-vapor contacting device (310) is connected to a heating device such as a reboiler (320) for evaporating a portion of the liquid-phase (301) exiting from the liquid-vapor contacting device (310) via the liquid phase effluent outlet (314).

The liquid phase effluent outlet (314) of the liquid-vapor contacting device (310) of the second liquid-vapor contacting apparatus (300) is preferably connected to a liquid phase effluent inlet (321) of the reboiler device (320) by a passage (301) suitable for conducting a liquid phase effluent stream (301) from the second liquid-vapor contacting device (310) to the reboiler device (320). Reboiler device (320) preferably has a liquid phase outlet (322) for recycling liquid phase components entering the reboiler device (320) back to the liquid-vapor contacting device (310) via liquid phase passage (323) through an inlet (328) of the liquid-vapor contacting device (310).

Reboiler device (320) is connected to the lower portion (312) of the liquid-vapor contacting device (310) for recycling a portion of the liquid phase (323) from the outlet (322) of the reboiler device (320) to the lower portion (312) of the liquid-vapor contacting device (310) via a recycle stream (301, 323) as recycle for the liquid-vapor contacting device (310). The reboiler device (320) may be located below, or integral with, the lower portion (312) of the liquid-vapor contacting device (310) to allow a liquid recycle phase to flow from the reboiler device (320) into the liquid-vapor contacting device (310).

A liquid-phase effluent outlet (324) of the reboiler (320) of the liquid-vapor contacting device (310) is also connected to a recycle inlet (115) of at least one dichlorohydrin dehydrochlorination reactor (110) via a suitable passage (325, 326) for recycling a liquid phase effluent (325, 325) from the reboiler (320) and liquid-vapor contacting device (310) to a reactor (110). Passage (325, 326) preferably has a purge (327) for removing impurities from the system.

Passage (325, 326) preferably does not comprise (i) a liquid-liquid phase separation device and/or (ii) a liquid-vapor contacting device.

The apparatus preferably comprises a device (not shown) for applying a vacuum to the liquid-vapor contacting devices (210, 310) for reducing the pressure in the liquid-vapor contacting devices (210, 310) below ambient atmospheric pressure. The device is preferably a steam-jet ejector or a vacuum pump.

The following examples are for illustrative purposes only and are not intended to limit the scope of the present invention.

Example

In this example, an ECH recovery process according to the present invention is simulated based data collected from prototyping experiments.

Referring to FIG. 1, stream 112 containing the crude ECH stream from the dichlorohyrin dehydrochlorination unit (110) enters the first finishing column (210) for light-boiling impurities and water removal. The column is operated at 0.4 atm (40 kPa) and contains 19 theoretical stages. The overhead vapor stream (202) is condensed using exchanger (230) which drains into a decanter (240). Stream (233) is the vent from the system containing non-condensables and lights. Two phases are formed in the decanter from the ECH—H$_2$O azeotrope. The aqueous stream (243) is recycled back to the dehydrochlorination unit (110) and the organic stream (245, 246) is refluxed back to the first finishing column (210). A small purge (247) is taken from the reflux to prevent buildup of lights. The heat input into the first finishing column is provided by the exchanger (220).

Stream (201, 224) from the bottom of the first finishing column is fed to the second finishing column (310). The second column is operated at 0.25 atm (25 kPa) and a bottom temperature of 106° C. and contains 18 theoretical stages. ECH is removed from the liquid phase as a vapor phase effluent stream (302), which is condensed by heat exchanger (330). Stream (333) is the vent from the second column (310). Part of the condensed vapor (335) is refluxed back to the column (310) via stream (336) and the remaining stream (338) is highly purified ECH substantially free of water and impurities.

The liquid phase effluent leaving the bottom of the column (310) via stream (301, 321, 322) containing the unreacted DCH from the dehydrochlorination process is recycled back to the dehydrochlorination process (100). A fraction of the ECH is intentionally permitted to remain in the liquid phase effluent stream in the bottom of the second finishing column to maintain the temperature of the column below 106° C. A small purge (323) is taken from the DCH recycle stream to prevent buildup of heavies (i.e., high boiling impurities). The heat input into the first finishing column is provided by the exchanger (320).

The results are presented in Table 1 below.

TABLE 2A

| | 106° C. | | |
|---|---|---|---|
| | 221 | 337 | 321 |
| Temperature (° C.) | 104 | 40 | 106 |
| Pressure (kPa) | 67 | 25 | 37 |
| ACRO | | | |
| H$_2$O | 1 ppm | 1 ppm | |
| ECH | 0.9877 | 0.9999 | 0.3590 |
| BCAA | 58 ppm | 22 ppm | 0.0019 |
| TCP | 879 ppm | | 0.0459 |
| 1,3-DCH | 349 ppm | | 0.0182 |
| 2,3-DCH | 0.0107 | | 0.5596 |
| DCOPP | 294 ppm | | 0.0154 |

TABLE 2C

| | 130° C. | | |
|---|---|---|---|
| | 221 | 337 | 321 |
| Temperature (° C.) | 104 | 40 | 130 |
| Pressure (kPa) | 67 | 25 | 37 |
| ACRO | | | |
| H$_2$O | 1 ppm | 1 ppm | |
| ECH | 0.9875 | 0.9999 | 0.0997 |
| BCAA | 58 ppm | 43 ppm | 0.0011 |
| TCP | 945 ppm | | 0.0686 |
| 1,3-DCH | 353 ppm | | 0.0256 |

TABLE 1

Epichlorohydrin Purification Computer Simulation Data

| Stream | 102 | 202 | 235 | 245 | 246 | 247 | 243 | 225 | 302 |
|---|---|---|---|---|---|---|---|---|---|
| Temperature (° C.) | 30 | 86 | 30 | 30 | 31 | 31 | 30 | 104 | 76 |
| ACRO | 431 ppm | 0.0341 | 0.0341 | 0.0349 | 0.0349 | 0.0349 | 0.0084 | | |
| H2O | 0.0181 | 0.0532 | 0.0532 | 0.0193 | 0.0193 | 0.0193 | 0.9271 | 1 ppm | 1 ppm |
| ECH | 0.9694 | 0.9102 | 0.9102 | 0.9458 | 0.9458 | 0.9458 | 0.0644 | 0.9877 | 1.0000 |
| BCAA | 57 ppm | | | | | | | 58 ppm | 22 ppm |
| TCP | 859 ppm | | | | | | | 879 ppm | |
| 1,3-DCH | 341 ppm | | | | | | | 349 ppm | |
| 2,3-DCH | 0.0105 | | | | | | | 0.0107 | |
| DCOPP | 288 ppm | | | | | | | 294 ppm | |

| Stream | 335 | 336 | 338 | 325 | 326 | 327 | 233 | 333 |
|---|---|---|---|---|---|---|---|---|
| Temperature (° C.) | 40 | 40 | 40 | 106 | 106 | 106 | 30 | 40 |
| ACRO | | | | | | | 0.0902 | |
| H2O | 1 ppm | 1 ppm | 1 ppm | | | | 0.0568 | |
| ECH | 1.0000 | 1.0000 | 1.0000 | 0.3590 | 0.3590 | 0.3590 | 0.1858 | 0.4540 |
| BCAA | 22 ppm | 22 ppm | 22 ppm | 0.0019 | 0.0019 | 0.0019 | | 4 ppm |
| TCP | | | | 0.0459 | 0.0459 | 0.0459 | | |
| 1,3-DCH | | | | 0.0182 | 0.0182 | 0.0182 | | |
| 2,3-DCH | | | | 0.5596 | 0.5596 | 0.5596 | | |
| DCOPP | | | | 0.0154 | 0.0154 | 0.0154 | | |

(stream numbers correspond to the line numbers in FIG. 1)
(all concentrations are in weight fractions unless otherwise specified)

The above simulation uses acrolein (ACRO) to represent the lights, 2-chloroallyl alcohol (BCAA) and 1,2,3-trichloro-propane (TCP) to represent intermediate boilers and dichlorooxy-propoxy-propane (DCOPP) to represent heavies.

Computer simulation examples showing the relationship between the fractions of ECH vaporized to the temperature in the second finishing column are shown in Tables 2A, 2B, and 2C below.

TABLE 2C-continued

| | 130° C. | | |
|---|---|---|---|
| | 221 | 337 | 321 |
| 2,3-DCH | 0.0108 | | 0.7835 |
| DCOPP | 296 ppm | | 0.0215 |

TABLE 2B

| | 120° C. | | |
|---|---|---|---|
| | 221 | 337 | 321 |
| Temperature (° C.) | 104 | 40 | 120 |
| Pressure (kPa) | 67 | 25 | 37 |
| ACRO | | | |
| $H_2O$ | 1 ppm | 1 ppm | |
| ECH | 0.9876 | 0.9999 | 0.1838 |
| BCAA | 58 ppm | 34 ppm | 0.0016 |
| TCP | 930 ppm | | 0.0614 |
| 1,3-DCH | 351 ppm | | 0.0232 |
| 2,3-DCH | 0.0108 | | 0.7105 |
| DCOPP | 295 ppm | | 0.0195 |

As can be seen from the above computer simulation data, the higher the level of ECH in the bottom stream (lower ECH vaporization) results in lower temperature in the column and also lower impurities in the purified ECH stream (337) for a given pressure.

What is claimed is:

1. A process for purifying epichlorohydrin comprising:
   (1) distilling and/or fractionating a feed stream comprising epichlorohydrin, dichlorohydrin(s), up to 5 weight-percent of one or more substances other than dichlorohydrin having a boiling point at the distillation and/or fractionation pressure that is higher than the boiling point or epichlorohydrin at the same pressure, and optionally one or more substances other than epichlorohydrin having a boiling point at the distillation and/or fractionation pressure that is lower than or equal to the boiling point of epichlorohydrin at the same pressure, wherein the distillation and/or fractionation is carried out at a pressure below atmospheric pressure and temperature sufficient to separate a vapor phase effluent comprising epichlorohydrin from a liquid phase effluent comprising dichlorohydrin(s), epichlorohydrin, and one or more substances other than epichlorohydrin and dichlorohydrin; wherein the distillation/fractionation of this step (1) is conducted at a temperature not greater than 150° C.; and wherein the distillation/fractionation of this step (1) is carried out to retain at least 5 weight-percent epichlorohydrin in the liquid effluent stream produced by this step (1);
   (2) passing at least a portion of the liquid effluent stream produced in step (1) directly to a dichlorohydrin dehydrochlorination process, and subjecting the at least a portion of the liquid phase effluent of step (1) to a dichlorohydrin dehydrochlorination process for converting the dichlorohydrin(s) present in the liquid phase effluent to epichlorohydrin; and
   (3) recovering the vapor phase effluent of step (1) comprising purified epichlorohydrin.

2. The process according to claim 1 including removing one or more substances other than epichlorohydrin and dichlorohydrin(s) from at least a portion of the liquid phase effluent of step (1).

3. The process according to claim 1, wherein the distillation/fractionation of step (1) is conducted at a temperature not greater than 130° C.

4. The process according to claim 1 or claim 2, wherein the feed stream of step (1) comprises at least 10 weight-percent dichlorohydrin(s), up to 2 weight-percent of one or more substances other than dichlorohydrin having a boiling point higher than the boiling point of epichlorohydrin, less than 0.1 weight-percent of one or more substances other than epichlorohydrin having a boiling point lower than or equal to the boiling point of epichlorohydrin, and a balance comprising epichlorohydrin.

5. The process according to claim 1 or claim 2, wherein the feed stream of step (1) is a liquid phase effluent stream produced by distilling and/or fractionating a feed stream comprising a dichlorohydrin dehydrochlorination process effluent stream comprising epichlorohydrin, dichlorohydrin(s), one or more substances having a boiling point higher than the boiling point of epichlorohydrin and one or more substances having a boiling point lower than the boiling point of epichlorohydrin under distillation/fractionation temperature and pressure conditions sufficient to separate the feed stream into a vapor phase effluent comprising epichlorohydrin and one or more substances in the feed stream having a boiling point lower than the boiling point of epichlorohydrin and a liquid phase effluent stream comprising epichlorohydrin, dichlorohydrin(s), and one or more substances other than dichlorohydrin having a boiling point higher than the boiling point of epichlorohydrin, and optionally one or more substances having a boiling point lower than epichlorohydrin.

6. The process according to claim 5, wherein the one or more substances having a boiling point lower than the boiling point of epichlorohydrin comprises water and at least a portion of the epichlorohydrin and water removed from the dehydrochlorination process effluent stream is recycled to the dichlorohydrin dehydrochlorination process.

7. A process for producing epichlorohydrin comprising:
   (a) contacting a feed stream comprising dichlorohydrin(s) and/or ester(s) thereof and one or more substances other than dichlorohydrin(s) and/or ester(s) thereof with a base in the presence of water under dichlorohydrin dehydrochlorination conditions to produce a dehydrochlorination effluent stream comprising epichlorohydrin, unconverted dichlorohydrin(s), one or more substances other than epichlorohydrin and dichlorohydrin(s) having a boiling point higher than the boiling point of epichlorohydrin and one or more substances other than epichlorohydrin and dichlorohydrin(s) having a boiling point lower than the boiling point of epichlorohydrin;
   (b) distilling and/or fractionating the dehydrochlorination effluent stream of step (a) at a pressure below atmospheric pressure and temperature sufficient to separate a vapor effluent stream comprising epichlorohydrin and one or more substances other than epichlorohydrin having a boiling point lower than or equal to the boiling point of epichlorohydrin from a liquid effluent stream comprising epichlorohydrin, dichlorohydrin(s), and one or more substances other than dichlorohydrin(s) having a boiling point higher than the boiling point of epichlorohydrin; and
   (c) using at least a portion of the liquid effluent stream of step (b) as the feed stream in the process according to claim 1 or claim 2.

8. An apparatus for producing purified epichlorohydrin comprising:
   (1) a dehydrochlorination apparatus for conducting dichlorohydrin(s) dehydrochlorination comprising one or more reactor vessels, at least one feed stream inlet, at least one steam inlet for connection to a steam source, at least one dehydrochlorination product effluent outlet, and optionally one or more steam stripping columns connected between the one or more reactors and the at least one dehydrochlorination product effluent outlet;

(2) a first liquid-vapor contacting apparatus for distilling a mixture comprising epichlorohydrin, dichlorohydrin(s), one or more substances other than dichlorohydrin(s) having a boiling point higher than epichlorohydrin and one or more substances other than epichlorohydrin having a boiling point lower than or equal to epichlorohydrin comprising a liquid-vapor contacting device, a heating or evaporating apparatus for heating or evaporating a liquid in the lower portion of the liquid-vapor contacting device and a cooling apparatus for condensing epichlorohydrin and one or more substances having a boiling point lower than epichlorohydrin, the liquid-vapor contacting device having an upper portion, a lower portion, a vapor phase effluent outlet in the upper portion, a liquid phase effluent outlet in the lower portion, and at least one feed stream inlet between the vapor phase effluent outlet and the liquid phase effluent outlet and the cooling apparatus comprising one or more cooling devices and, optionally, one or more vapor purges; and (3) a second liquid-vapor contacting apparatus for distilling a mixture comprising epichlorohydrin, dichlorohydrin(s), one or more substances other than dichlorohydrin(s) having a boiling point higher than epichlorohydrin and optionally less than 0.1 weight-percent of one or more substances other than epichlorohydrin having a boiling point lower than or equal to epichlorohydrin comprising a liquid-vapor contacting device, a heating or evaporating apparatus for heating or evaporating a liquid in the lower portion of the liquid-vapor contacting device and a cooling apparatus for condensing epichlorohydrin, the liquid-vapor contacting device comprising an upper portion, a lower portion, a vapor phase effluent outlet in the upper portion, a liquid phase effluent outlet in the lower portion, and at least one feed stream inlet between the vapor phase effluent outlet and the liquid phase effluent outlet and the cooling apparatus comprising one or more cooling devices and, optionally one or more vapor purges;

wherein the dehydrochlorination product effluent outlet of the dehydrochlorination apparatus is connected to the feed stream inlet of the liquid-vapor contacting device of the first liquid-vapor contacting apparatus by a passage suitable for conducting dichlorohydrin dehydrochlorination reactor effluent from the dichlorohydrin dehydrochlorination apparatus to the liquid-vapor contacting device of the first liquid-vapor contacting apparatus;

the liquid phase effluent outlet of the first liquid-vapor contacting apparatus is connected to the teed stream inlet of the liquid-vapor contacting device of the second liquid-vapor contacting apparatus by a passage suitable for conducting liquid phase effluent from the liquid-vapor contacting device of the first liquid-vapor contacting apparatus to the liquid-vapor contacting device of the second liquid-vapor contacting apparatus; and the liquid phase effluent outlet of the liquid-vapor contacting device of the second liquid-vapor contacting apparatus is connected to one or more reactor(s) of the dichlorohydrin dehydrochlorination apparatus by a passage suitable for conducting a liquid phase effluent from the liquid-vapor contacting device of the second liquid-vapor contacting apparatus to the one or more reactor(s) of the dichlorohydrin dehydrochlorination apparatus.

9. The apparatus of claim 8, wherein the apparatus further comprises;

(4) a liquid-liquid phase separation apparatus for separating a liquid phase effluent stream comprising water and one or more substantially organic compounds into an aqueous phase effluent stream and an organic phase effluent stream comprising at least one liquid-liquid phase separation device, a liquid phase effluent inlet, an aqueous liquid phase effluent outlet and an organic liquid phase effluent outlet;

wherein the condensed liquid phase effluent stream outlet of cooling device is associated with the liquid phase effluent stream inlet of the liquid-liquid phase separation device for conducting a condensed liquid phase effluent from the cooling device to the liquid-liquid phase separation device;

the aqueous liquid phase effluent stream let of the liquid-liquid phase separation device is connected to one or more reactors of the dichlorohydrin dehydrochlorination, apparatus by a passage suitable for conducting an aqueous liquid phase effluent stream from the liquid-liquid phase separation device to one or more of the reactors of the dichlorohydrin dehydrochlorination apparatus; and the organic liquid phase effluent stream outlet of the liquid-liquid phase separation device is connected to the top portion of the liquid-vapor contacting device of the first liquid-vapor contacting apparatus by a passage suitable for conducting an organic liquid phase effluent stream from the liquid-liquid phase separation device to the first liquid-vapor contacting apparatus.

10. The apparatus of claim 9, wherein the cooling device is a condenser and the liquid-liquid phase separation device is a decanter.

11. The apparatus of any one of claims 8 to 10, wherein the liquid-vapor contacting device is a distillation column.

\* \* \* \* \*